US006506365B1

(12) United States Patent
Redl et al.

(10) Patent No.: US 6,506,365 B1
(45) Date of Patent: Jan. 14, 2003

(54) FIBRIN/FIBRINOGEN BINDING CONJUGATE

(75) Inventors: Heinz Redl, Vienna (AT); Walter Fuerst, Vienna (AT); Rudolf Kneidinger, Vienna (AT)

(73) Assignee: Baxter Aktiengesellschaft, Vienna (AT)

(*) Notice: Subject to any disclaimer, the term of this patent is extended or adjusted under 35 U.S.C. 154(b) by 0 days.

(21) Appl. No.: 09/669,240

(22) Filed: Sep. 25, 2000

(51) Int. Cl.[7] .......................... A61K 38/16; A61K 38/18; A61K 38/36; A61K 39/44; C07K 14/00

(52) U.S. Cl. ...................... 424/9.4; 424/1.69; 424/9.34; 424/178.1; 424/426; 514/2; 514/8; 514/12; 514/21; 514/44; 530/391.1; 530/402; 530/410

(58) Field of Search .............................. 424/1.49, 1.53, 424/1.69, 9.34, 9.341, 9.4, 9.411, 178.1, 179.1, 180.1, 181.1, 182.1, 425, 426, 484, 486; 514/2, 8, 12, 21, 43, 44; 530/382, 391.1, 391.3, 391.5, 391.7, 391.9, 402, 408, 409, 410; 536/23.1

(56) References Cited

U.S. PATENT DOCUMENTS

| | | | |
|---|---|---|---|
| 4,359,049 A | 11/1982 | Redl et al. | 604/82 |
| 4,393,041 A | * 7/1983 | Brown et al. | 424/426 |
| 4,631,055 A | 12/1986 | Redl et al. | 604/82 |
| 4,735,616 A | 4/1988 | Eibl et al. | 604/191 |
| 5,217,705 A | * 6/1993 | Reno et al. | 424/1.1 |
| 5,328,996 A | * 7/1994 | Boyle et al. | 536/23.1 |
| 5,332,671 A | 7/1994 | Ferrara et al. | 435/240.1 |
| 5,364,612 A | * 11/1994 | Goldenberg | 424/1.53 |
| 5,792,742 A | * 8/1998 | Gold et al. | 514/2 |

FOREIGN PATENT DOCUMENTS

| | | |
|---|---|---|
| CA | 1 168 982 | 6/1984 |
| EP | 0 292 472 B1 | 11/1988 |
| WO | WO98/43686 A1 | 10/1998 |
| WO | WO01/10479 A1 | 2/2001 |

OTHER PUBLICATIONS

Kurokawa et al. Enhanced Fibrinolysis By A Bispecific Monoclonal . . . Bio/Technology, vol. 7, pp. 1163–1167, Nov. 1989.*

Frank et al., "Leptin enhances wound re–epithelialization and constitutes a direct function of leptin in skin repair," *The Journal of Clinical Investigation*, 106(4):501–509 (2000).

Houck et al., "Dual Regulation of Vascular Endothelail Growth Factor Bioavailability by Genetic and Proteolytic Mechanisms," *The Journal of Biological Chemistry*, 267(36):26031–26037 (1992).

Markland et al., "Iterative Optimization of High–Affinity Protease Inhibitors Using Phase Display, 1. Plasmin," *Biochemistry*, 35:8045–8057 (1996).

Sahni et al., "Vascular Endothelial Growth Factor Binds to Fibrinogen and Fibrin and Stimulates Endothelial Cell Proliferation" *Blood*, 96:3772–3778 (2000).

Sierra–Honigmann et al., "Biological Action of Leptin as an Angiogenic Factor," *Science*, 281:1683–1686 (1998).

Tischer et al., "The Human Gene for Vascular Endothelial Growth Factor," *Journal of Biological Chemistry*, 266(18):11947–11954 (1991).

* cited by examiner

*Primary Examiner*—Jeffrey E. Russel
(74) *Attorney, Agent, or Firm*—Annette S. Parent; Janice Guthrie

(57) ABSTRACT

The invention relates to fibrin/fibrinogen binding conjugate comprising a fibrin/fibrinogen binding moiety, a substance capturing moiety capable of reversibly binding to a pharmaceutically active substance, and a pharmaceutically active substance, wherein the fibrin/fibrinogen binding moiety is bound to the substance capturing moiety, a kit for forming a depot for a pharmaceutically active substance and a method for producing a depot for a pharmaceutically active substance.

22 Claims, 5 Drawing Sheets

FIBRIN/FIBRINOGEN BINDING CONJUGATE

FIELD OF THE INVENTION

The present invention relates to conjugates having specific utility as depots for pharmaceutically active substances.

BACKGROUND OF THE INVENTION

Providing drug depots for sustained-release action is essential for efficient treatment of patients which require a steady administration of specific pharmaceutically active substances, especially if the drug is desired to be applied inside the body. A prerequisite for an adequate drug depot is that the release of the pharmaceutically active substance from such a depot is controllable by specific retardation processes. This implies that the pharmaceutically active substance has to be connected to the depot matrix either in a reversible or an irreversible way.

The matrix to which the pharmaceutically active substance is bound should not only have an affinity to the active substance but also have biocompatible properties. Preferably, such depot matrices are biodegradable within the body of the patient so that no further treatment of the patient for removing the emptied depot is necessary.

Because of its advantageous biological properties especially fibrin gels have been proposed as preferred drug depot matrices (see e.g. AT 369 900). Fibrin gels are easy to prepare, have good biocompatibility and their biological degradation inside the body can be easily regulated. However, due to the hydrated and wide porous structure of fibrin, diffusion of pharmaceutically active substances occurs with a rate much too fast for most purposes even if the fibrin gel is highly cross-linked by excess addition of its natural cross-linking effector, factor XIII.

In preliminary experiments carried out for the present invention it could be shown that different proteins, such as β-Galactosidase are completely released from a fibrin gel within three days or even less.

It has therefore been proposed to covalently link bioactive factors to a fibrin network by linking a transglutaminase substrate domain to a bioactive factor using factor XIIIa activity (WO98/43686). However, covalent binding of the drug of interest to the fibrin network may result in binding too strong to allow sufficient release of the drug to the patient. Also not all drugs do allow covalent binding; moreover, a stability problem for fibrin might arise because cross-linking sites are taken away by the transglutaminase substrates involved. The presence of transglutaminase is essential for this reaction.

It is therefore an object to provide a drug depot having satisfactory biocompatibility and a half-life in the patient life which may efficiently be regulated.

It is a further object of the present invention to provide for an alternative drug depot based on fibrin, especially without altering the active substance or using enzymatic activity for the linkage.

Another object of the present invention is to provide a drug depot with efficient retardation capacity of the biologically active substance to be administered to a patient over a prolonged period of time compared to the release time of this drug by diffusion from a standard fibrin gel.

SUMMARY OF THE INVENTION

These objects are solved by a fibrin/fibrinogen binding conjugate comprising a fibrin/fibrinogen binding moiety, a substance capturing moiety capable of reversibly binding to a pharmaceutically active substance, and a pharmaceutically active substance, wherein said fibrin/fibrinogen binding moiety is bound to said substance capturing moiety.

With the conjugate according to the present invention the affinity of binding partners to fibrin or fibrinogen are used to link binding partners of pharmaceutically active substances to a fibrin gel. Due to these fibrin or fibrinogen binding moieties, the conjugates are bound efficiently enough to the fibrin matrix so that elution of the pharmaceutically active substance is not possible by simple diffusion but mainly dependent on the affinity of the fibrin/fibrinogen binding moiety to fibrin and on the binding affinity of the substance capturing moiety to the pharmaceutically active substance.

The binding of the fibrin/fibrinogen binding moiety to the substance capturing moiety can be covalently, e.g. via linkers as known from the state of the art, or by electrostatic forces.

The term "fibrin/fibrinogen binding moiety" relates to a binding moiety which is capable of binding to fibrin or to fibrinogen and fibrin. It is essential that the binding capacity is at least present for the fibrin and it is preferred if this binding capacity is also given for the fibrinogen molecule. For the latter case it is then possible to form the fibrin gel with fibrinogen molecules which are already "loaded" with the conjugates according to the present invention to allow a homogeneous forming of the drug depot and a homogeneous distribution of the conjugate according to the present invention (and therefore the drug) throughout the fibrin drug depot.

DETAILED DESCRIPTION OF THE INVENTION

Figure 1:
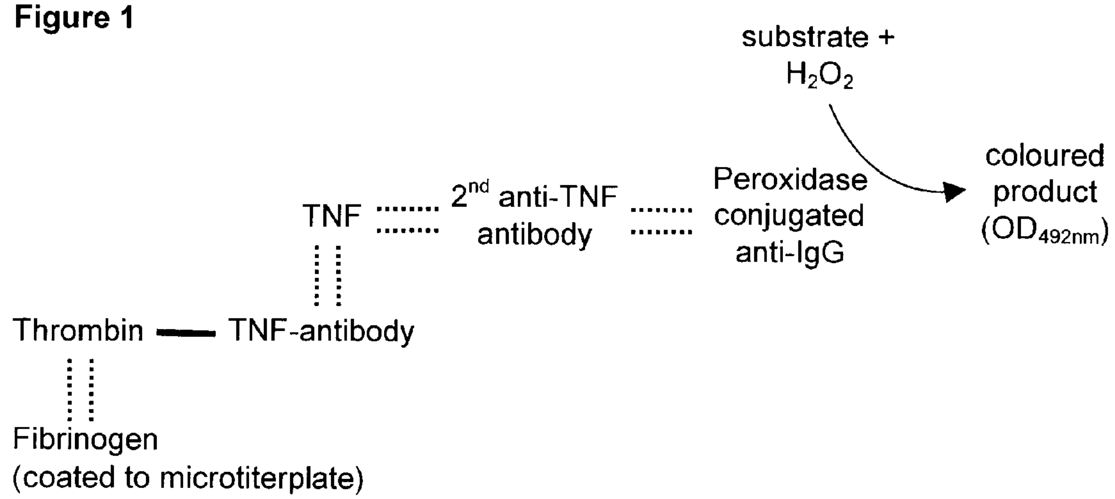
FIG. 1 shows the ELISA-sandwich system for the detection of the covalent binding (–) of TNF antibody and thrombin as well as the binding affinities ( : : : ) to fibrin/fibrinogen and TNF, respectively.

The present invention provides for a useful biomatrix using a conjugate which is able to bind to a fibrin gel or to fibrinogen and retains such binding affinity after cleaving the fibrinogen to fibrin.

The conjugate according to the present invention comprises: a binding moiety which safeguards the binding to fibrin/fibrinogen, a moiety which is capable of binding to a pharmaceutically active substance and the pharmaceutically active substance. According to the present invention the fibrin/fibrinogen binding moiety is bound to the substance capturing moiety, preferably covalently. For example a fibrin/fibrinogen binding protein or a part thereof which binds to fibrin/fibrinogen may be bound or coupled to a substance capturing moiety. This coupling may be realized e.g. by chemical linkers, by recombinant DNA technology, by peptide synthesis or combinations of these techniques.

The fibrin/fibrinogen binding moiety may be derived from naturally occuring (e.g. physiological) binding proteins, such as thrombin, fibronectin, bacterial fibrinogen binding proteins, basic fibroblast growth factor, integrins, tissue-type plasminogen activator and similar proteins exhibiting at least one fibrin/fibrinogen binding moiety. For the present conjugate these proteins may either be used in their physiological form or in a processed form. For example, such physiological binding partners may be processed by known biochemical techniques, in order to provide at least the fibrin/fibrinogen binding parts of these proteins. Alternatively, the parts known to bind to fibrin/fibrinogen can also be provided by recombinant DNA technology. Since for many fibrin/fibrinogen binding proteins a three-dimensional structure has been described or proposed, any man skilled in the art can immediately select those parts of these proteins which are relevant for fibrin/fibrinogen binding within the course of the present invention. Other substances with binding affinity for fibrin/fibrinogen may be analyzed for their putative fibrin/fibrinogen binding sites based on known three-dimensional models of the above mentioned proteins, e.g. by sequence analysis, if such substances are proteins or protein derivatives or selection by phage display.

The choice of the substance capturing moiety or the directly bound pharmaceutically active substance is essentially dependent on the pharmaceutically active substance to be administered by the fibrin depot. Suitable pairs of substance capturing moieties and pharmaceutically active substances are known to the skilled man in the art and may easily be adapted for the present invention.

For example a substance capturing moiety may be an antibody which specifically recognizes and binds the pharmaceutically active substance of interest (e.g. as a antigen). Under "antibody" within the course of the present invention a complete antibody of any class, comprising the constant domain as well as the variable antigen binding domain but also parts of antibodies or antibody derived molecules, e.g. fragments or recombinant constructs, may be used as a substance capturing moiety according to the present invention. Indeed, most of the parts of such "classical" antibodies may be omitted if necessary as long as the essential moiety, namely the variable binding region which allows the binding of the pharmaceutically active substance, is present.

A further example of a substance capturing moiety may be the group of antibody binding molecules, e.g. bacterial proteins like protein A or protein G or Fc-receptor of macrophages, as well as fragments or recombinant constructs thereof.

According to a preferred embodiment of the present invention monoclonal antibodies or the antigen binding regions of monoclonal antibodies are used as substance capturing moieties. These antibodies or antibody parts may easily be prepared and manipulated by the skilled man in the art. Further, coupling of such a monoclonal antibody or parts thereof to a fibrin/fibrinogen binding moiety, especially a fibrin binding protein, may be established by classical protein chemistry.

The present invention may be adapted for all pharmaceutically active substances possible, especially for those for which a suitable binding partner is already known (e.g. antigen/antibody, receptor/ligand, complex partners). In each case, the binding partner to be applied as a drug is bound to the conjugate according to the present invention only via its individual corresponding binding partner, the latter being covalently coupled to the fibrin/fibrinogen binding moiety.

Preferred pharmaceutically active substances to be added in the conjugate according to the present invention are antibiotics, growth factors, receptors for tissue components, tissue adhesive substances, anti-tumor agents, cell adhesive substances, nucleic acids, plasma proteins, antiproteases, fibrinolysis inhibitors, hormones, heparinoids and mixtures thereof. These substances may either be directly pharmaceutically active or allow an improved action of another pharmaceutically active substance which. may be applied simultaneously or not with the present drug depot. For example, receptors for tissue components or tissue adhesive substances may be applied which allow an improved performance of a tissue adhesive based on fibrinogen. Other examples which change the adhesive properties of a tissue adhesive are substances which may be provided with the present conjugate. If applied together with a "classical" tissue adhesive, the presence of such pharmaceutically active substances which have an influence on the adhesion properties may influence the adhesive or non-adhesive capacity of the fibrinogen tissue adhesive to specific tissues or cells. Other substances, such as nucleic acids or anti-tumor agents may also be applied together with a specific fibrin/fibrinogen basis to form a depot for these substances at the site necessary for a desired effect. Also substances useful for image based diagnostic methods e.g. for X-rays or magnetic resonance induction (MRI) or colors may be used according to the present invention.

According to a preferred embodiment of the present invention the conjugate or the bifunctional molecule is designed for the incorporation in a "classical" tissue adhesive system. Such a system usually comprises a fibrinogen and a thrombin containing preparation similar to a "one-" or "two component" glue resulting in fibrin formation at the site of application or a preformed fibrin preparation, e.g. a fibrin fleece. The formed fibrin clot or the fibrin fleece allows e.g. wound closure or tissue adhesion. Further ingredients in this system are e.g. Factor XIII (as a cross-linker), fibrinolysis inhibitors, etc (see e.g. Fibrin Sealing in Surgical and Non-Surgical Fields, Schlag G. Redl H. editors, Vols. 1–9).

The fibrin/fibrinogen binding moiety and the substance capturing moiety are preferably covalently bound by a linker substance, especially linker substances which are used and have proven to be successfully applied in protein chemistry. This preferred embodiment is especially suited if enhanced flexibility of the moieties is desired.

Although the pharmaceutically active form of the conjugate according to the present invention comprises the pharmaceutically active substance, the present invention also relates to the conjugate without the drug. Such a "naked" conjugate may be easily transformed into a pharmaceutically active form by "loading" the conjugate comprising the fibrin/fibrinogen binding moiety and the substance capturing moiety with the individual drug wherefor the substance capturing moiety has been designed.

A specific embodiment of the present invention relates to a conjugate wherein the drug to be applied has been designed to carry a fibrin/fibrinogen containing moiety. According to this aspect of the present invention, the substance capturing moiety may be omitted. Also this conjugate may be designed by protein chemistry, peptide synthesis and/or recombinant technology by combining a fibrin/fibrinogen binding moiety with the pharmaceutically active substance, e.g. by direct covalent binding or by binding with suitable linker substances. Also these conjugates, which do not need a separate "loading" with the pharmaceutically active substance, may be used in a common tissue adhesive system as described above.

According to another aspect the present invention relates to a kit for forming a depot for a pharmaceutically active substance comprising a tissue adhesive based on fibrinogen and a conjugate according to the present invention. The conjugate may be provided in a separate form ready to be mixed before medical use. The "ready to use" mixture of the tissue adhesive based on fibrinogen and the conjugate according to the present invention may be applied with means and methods as already known in the art for "classical" tissue adhesives, especially with the fibrinogen component of such adhesives. This fibrinogen component may be mixed in a known way with a component containing an activity for processing fibrinogen to fibrin, preferably a thrombin preparation.

A kit according to the present invention may therefore also contain suitable devices for administering the tissue adhesive and the conjugate and optionally the fibrinogen to fibrin processing activity. Examples for such devices are described in EP 0 037 393 A, EP 0 315 222 A, EP 0 156 098 A, EP 0 210 160 A and EP 0 292 472 A, which are incorporated herein by reference.

According to another aspect the present invention relates to a method for producing a depot of a pharmaceutically active substance comprising

- providing a conjugate according to the present invention,
- administering this conjugate at a depot site together with a fibrinogen preparation,
- allowing processing of said fibrinogen to fibrin whereby a fibrin clot is formed, and
- allowing binding of the conjugate to said fibrinogen or the fibrin clot formed.

Processing of the fibrinogen to fibrin may either be performed by thrombin already being present at the site of administration or by an exogeneously added fibrinogen processing activity. Apart from thrombin or thrombin derived proteases, other proteases such as streptylase, protease III and venom proteases like e.g. baxotropin, may be used for cleaving the fibrinogen molecule. The binding of the conjugate to fibrin/fibrinogen may take place after forming of the fibrin clot. However, it is preferred to allow this binding process at an earlier stage, e.g. during the fibrinogen processing step or (most preferred) even before, so that binding of the conjugate according to the present invention takes place at the fibrinogen level. This results in a fibrin depot which has a homogeneous distribution of conjugate throughout the whole depot. On the other hand, if the conjugate is intended to be located mainly on the surface of the fibrin depot, binding of the conjugate should be allowed after forming of the fibrin clot.

Another aspect of the present invention relates to a depot for a pharmaceutically active substance, comprising a conjugate according to the present invention and fibrin (e.g. a suitable fibrin matrix). Such a depot is e.g. obtainable by administration of a conjugate according to the present invention to a fibrin network basis.

Yet still another object of the present invention is drawn to a method for treating a patient suffering from a pathological state, said pathological state being treatable with a pharmaceutically active substance, comprising administering to this patient an effective amount of a tissue adhesive based on fibrinogen and a conjugate according to the present invention.

Thereby a depot of the pharmaceutically active substance with suitable releasing properties is provided which allows a suitable treatment of the patient with the pharmaceutical substance without the need of continuously and separately providing this substance.

The invention will now be explained in more detail by way of the examples and drawing figures to which, however, it shall not be restricted.

EXAMPLES

Within the present examples tumor necrosis factor (TNF) as an example for any pharmaceutically active substance is coupled via a commerically available TNF antibody to a fibrin binding substance. Thrombin and fibronectin have been selected as examples for substances having a fibrin/fibrinogen binding moiety. Coupling of the antibody to thrombin and fibronectin has been achieved with 1-ethyl-3-3-dimethyl-aminopropylcarbodiimid (EDC). With this type of reaction the carboxy groups of a coupling component have been activated with EDC; these activated carboxy groups react with amino groups of the other component. Since the properties of the moieties may be different depending on which component is activated first, always both possibilites or variations have been investigated. In the following examples conjugate A-B means that component A is the component which is activated at the carboxy groups and component B is bound via its amino group. The proof of a successful coupling and the detection of the individual binding affinities (TNF-antibody, thrombin/fibronectin-fibrin) was analyzed via sandwich-ELISA.

Example 1

Coupling of TNF Antibody to Thrombin

Figure 2:
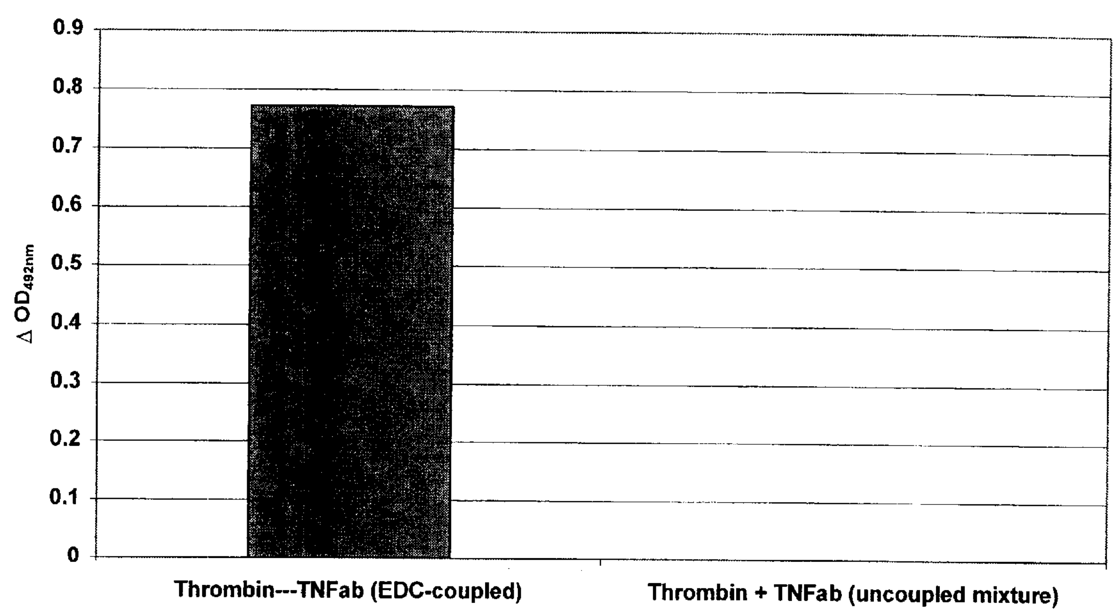
FIG. 2 shows the binding of TNF to a fibrinogen matrix via a TNF antibody coupled to thrombin.

A commercially available TNF antibody was coupled to thrombin via EDC. The proof for coupling and the individual binding affinities in the conjugates was detected via sandwich-ELISA (FIG. 1). Briefly, a microtiter plate was coated with fibrinogen and subsequently incubated with a complex (thrombin-TNF antibody or TNF antibody-thrombin), with TNF, with a secondary TNF antibody and with an enzyme conjugate against the secondary antibody. This enzyme is responsible in the last step of the ELISA-method for transforming a colorless substrate to a colored compound which is subsequently detectable. The turnover of the substrate is only possible if both components (TNF antibody and thrombin) have been covalently coupled by the EDC reaction and both binding affinities have been preserved. Thrombin-TNF antibody as well as TNF antibody-thrombin give positive reaction in this system (FIG. 2). Unmodified TNF antibody used as control could not bind TNF to the fibrinogen matrix.

Example 2

Coupling of TNF Antibody to Fibronectin

Figure 3:
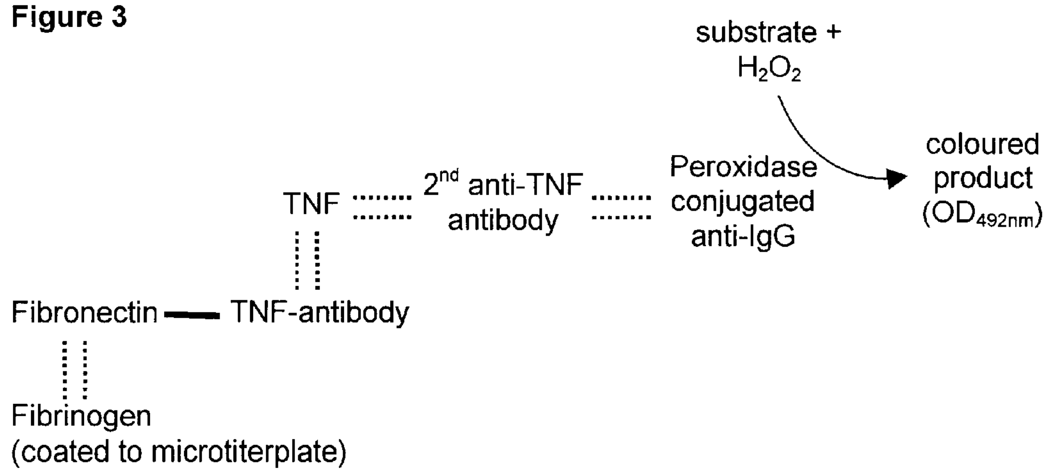
FIG. 3 shows the ELISA-sandwich system for the detection of covalent binding (–) of a TNF antibody and fibronectin and their binding affinities ( : : : ) to fibrin/fibrinogen and TNF, respectively.
Figure 4:
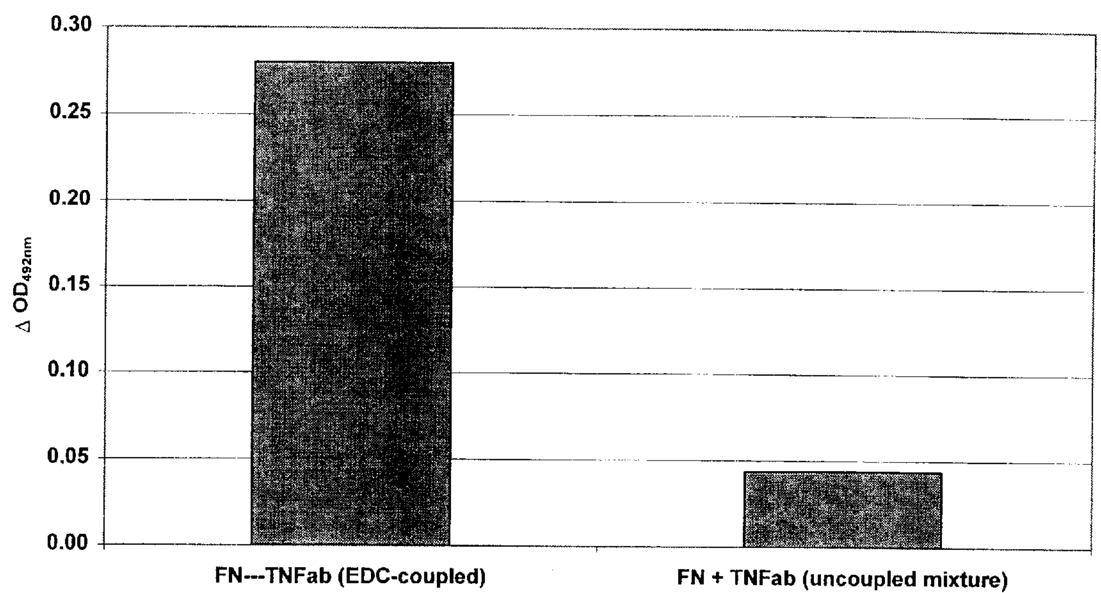
FIG. 4 shows the binding of TNF to a fibrinogen matrix via a TNF-antibody coupled to fibronectin.

A commercially available TNF antibody was coupled to fibronectin using EDC. The proof for coupling and the detection of the individual binding affinities in the conjugates was performed via sandwich-ELISA (FIG. 3), as in example 1. Fibronectin-TNF antibody as well as TNF antibody-fibronectin showed positive reaction in the present system (FIG. 4). A mixture of TNF antibody and fibronectin as control showed only a low binding of TNF to the fibrinogen matrix.

Example 3

Retarded Liberation of TNF From a Tissue Adhesive Clot

Figure 5:
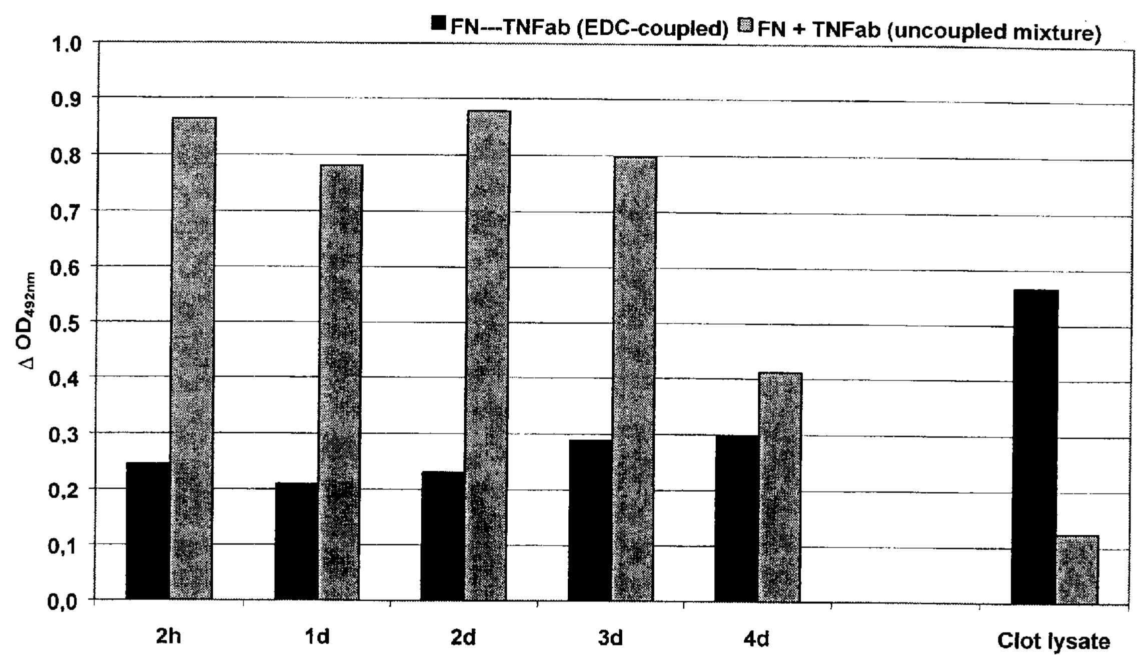
FIG. 5 shows the retention of uncoupled fibronectin using the conjugate according to the present invention compared to the-retention of TNF in the presence of uncoupled fibronectin and TNF antibody.

The proof for efficient retardation of TNF in a tissue adhesive clot based on fibrinogen was performed by adding TNF and fibronectin-TNF antibody complex as described in example 2 to the fibrinogen component of a fibrin sealant. In control experiments TNF and a mixture of fibronectin and TNF antibody have been added to this fibrinogen component. The fibrin clots were produced with such modified fibrinogen components and transferred to PBS 60 min after clotting. The clots then were incubated at 37° C. and PBS supernatants were substituted with fresh PBS at defined time periods. TNF content in these supernatants were detected (FIG. 5). After 12 days the clots were lysed with urokinase and the TNF content in the lysate was detected.

Addition of the fibronectin-TNF antibody complex to the fibrinogen component of the tissue adhesive resulted in a significant retardation of the liberation of TNF compared to the addition of a fibronectin+TNF antibody mixture. This was shown by reduced initial liberation of TNF in the PBS supernatants (days 1–3) as well as by a higher TNF content in the clot lysate after 12 days incubation in PBS (FIG. 5). Since fibrin clots have only been incubated in PBS and not been exposed to proteolytic digestion, the liberation of the TNF detected was mainly due to diffusion from the fibrin clot. Incubation with addition of proteases (e.g. urokinase) results in a continuous liberation of TNF over a longer period of time.

We claim:

1. Kit for forming a depot for a pharmaceutically active substance comprising a tissue adhesive based on fibrinogen and a fibrin/fibrinogen binding conjugate comprising a fibrin/fibrinogen binding moiety and a substance capturing moiety capable of reversibly binding to a pharmaceutically active substance, wherein said fibrin/fibrinogen binding moiety is bound to said substance capturing moiety.

2. Kit according to claim 1, further comprising a component containing an agent capable of processing fibrinogen to fibrin.

3. Kit according to claim 1, further comprising devices for administering said tissue adhesive and said conjugate to a depot site.

4. Method for producing a depot of a pharmaceutically active substance comprising providing a fibrin/fibrinogen binding conjugate comprising a fibrin/fibrinogen binding moiety, a substance capturing moiety capable of reversibly binding to a pharmaceutically active substance and a pharmaceutically active substance, wherein said fibrin/fibrinogen binding moiety is bound to said substance capturing moiety, administering said conjugate at a depot site together with a fibrinogen preparation, allowing processing of said fibrinogen to fibrin whereby a fibrin clot is formed, and allowing binding of said conjugate to said fibrinogen within said fibrin clot.

5. Method for producing a depot of a pharmaceutically active substance comprising providing a fibrin/fibrinogen binding conjugate comprising a fibrin/fibrinogen binding moiety, a substance capturing moiety capable of reversibly binding to a pharmaceutically active substance and a pharmaceutically active substance, wherein said fibrin/fibrinogen binding moiety is bound to said substance capturing moiety, administering said conjugate at a depot site together with a fibrinogen preparation, allowing processing of said fibrinogen to fibrin whereby a fibrin clot is formed, and allowing binding of said conjugate to said fibrin clot.

6. Method according to claim 4, wherein said processing of said fibrinogen to fibrin is performed by adding an agent capable of processing said fibrinogen to fibrin.

7. Method according to claim 6, wherein said agent is exogenous thrombin.

8. Depot for a pharmaceutically active substance comprising fibrin and a fibrin/fibrinogen binding conjugate comprising a fibrin/fibrinogen binding moiety, a substance capturing moiety capable of reversibly binding to a pharmaceutically active substance and a pharmaceutically active substance, wherein said fibrin/fibrinogen binding moiety is bound to said substance capturing moiety.

9. Depot for a pharmaceutically active substance, said depot obtainable by the steps comprising:

providing a fibrin/fibrinogen binding conjugate comprising a fibrin/fibrinogen binding moiety, a substance capturing moiety capable of reversibly binding to a pharmaceutically active substance and a pharmaceutically active substance, wherein said fibrin/fibrinogen binding moiety is bound to said substance capturing moiety, administering said conjugate at a depot site together with a fibrinogen preparation, allowing processing of said fibrinogen to fibrin whereby a fibrin clot is formed, and allowing binding of said conjugate to said fibrinogen or said fibrin clot.

10. Method for treating a patient suffering from a pathological state, said pathological state being treatable with a pharmaceutically active substance, comprising administering to said patient an effective amount of a tissue adhesive based on fibrinogen and a fibrin/fibrinogen binding conjugate comprising a fibrin/fibrinogen binding moiety, a substance capturing moiety capable of reversibly binding to said pharmaceutically active substance and said pharmaceutically active substance, wherein said fibrin/fibrinogen binding moiety is bound to said substance capturing moiety.

11. Kit according to claim 1, wherein said fibrin/fibrinogen binding moiety is selected from the group consisting of thrombin, fibronectin, bacterial fibrinogen binding proteins, basic fibroblast growth factor, tissue-type plasminogen activator, integrins, and molecules derived from any member of this group of proteins.

12. Kit according to claim 1, wherein said substance capturing moiety is an antibody which specifically recognizes said pharmaceutically active substance.

13. Kit according to claim 1, wherein said pharmaceutically active substance is selected from the group consisting of antibiotics, growth factors, receptors for tissue components, tissue adhesive substances, nucleic acids, plasma proteins, hormones, heparinoids, and imaging agents.

14. Kit according to claim 1, wherein said fibrin/fibrinogen binding moiety and said substance capturing moiety are covalently bound via a linker substance.

15. Method according to claim 4, wherein said fibrin/fibrinogen binding moiety is selected from the group consisting of thrombin, fibronectin, bacterial fibrinogen binding proteins, basic fibroblast growth factor, tissue-type plasminogen activator, integrins, and molecules derived from any member of this group of proteins.

16. Method according to claim 4, wherein said substance capturing moiety is an antibody which specifically recognizes said pharmaceutically active substance.

17. Method according to claim 4, wherein said pharmaceutically active substance is selected from the group consisting of antibiotics, growth factors, receptors for tissue components, tissue adhesive substances, nucleic acids, plasma proteins, hormones, heparinoids, and imaging agents.

18. Method according to claim 4, wherein said fibrin/fibrinogen binding moiety and said substance capturing moiety are covalently bound via a linker substance.

19. Depot according to claim 8, wherein said fibrin/fibrinogen binding moiety is selected from the group consisting of thrombin, fibronectin, bacterial fibrinogen binding proteins, basic fibroblast growth factor, tissue-type plasminogen activator, integrins, and molecules derived from any member of this group of proteins.

20. Depot according to claim 8, wherein said substance capturing moiety is an antibody which specifically recognizes said pharmaceutically active substance.

21. Depot according to claim 8, wherein said pharmaceutically active substance is selected from the group consisting of antibiotics, growth factors, receptors for tissue components, tissue adhesive substances, nucleic acids, plasma proteins, hormones, heparinoids, and imaging agents.

22. Depot according to claim 2, wherein said fibrin/fibrinogen binding moiety and said substance capturing moiety are covalently bound via a linker substance.

* * * * *